US009107971B2

(12) United States Patent
Coles

(10) Patent No.: US 9,107,971 B2
(45) Date of Patent: Aug. 18, 2015

(54) INTRACAVITY ULTRASOUND PROBE DISINFECTANT SYSTEM

(71) Applicant: Philip Coles, Deep River, CT (US)

(72) Inventor: Philip Coles, Deep River, CT (US)

(73) Assignee: PCI Medical, Inc., Deep River, CT (US)

( * ) Notice: Subject to any disclaimer, the term of this patent is extended or adjusted under 35 U.S.C. 154(b) by 0 days.

(21) Appl. No.: 14/268,344

(22) Filed: May 2, 2014

(65) Prior Publication Data
US 2014/0241942 A1 Aug. 28, 2014

Related U.S. Application Data

(62) Division of application No. 13/187,171, filed on Jul. 20, 2011, now Pat. No. 8,753,580.

(60) Provisional application No. 61/365,915, filed on Jul. 20, 2010.

(51) Int. Cl.
*A61L 9/00* (2006.01)
*A61L 2/00* (2006.01)
*A61L 2/18* (2006.01)
*A01N 1/02* (2006.01)
*A61B 8/12* (2006.01)
*A61B 8/00* (2006.01)
*A61K 8/22* (2006.01)
*A61K 33/00* (2006.01)
*A61L 12/00* (2006.01)
*B05C 3/00* (2006.01)
*B08B 3/00* (2006.01)

(52) U.S. Cl.
CPC ............... *A61L 2/186* (2013.01); *A01N 1/0215* (2013.01); *A61L 2/18* (2013.01); *A61B 8/12* (2013.01); *A61B 8/4422* (2013.01); *A61K 8/22* (2013.01); *A61K 33/00* (2013.01); *A61L 2/00* (2013.01); *A61L 12/00* (2013.01); *A61L 2202/14* (2013.01); *B05C 3/00* (2013.01); *B08B 3/00* (2013.01)

(58) Field of Classification Search
CPC ........ A01N 1/0215; A61L 2/00; A61L 12/00; A61K 8/22; A61K 33/00; B05C 3/00; B08B 3/00
USPC ........ 134/84, 93, 94.1; 422/1, 28, 32, 36, 292
See application file for complete search history.

(56) References Cited

U.S. PATENT DOCUMENTS

| 4,892,706 A | 1/1990 | Kraovic et al. |
| 5,225,160 A | 7/1993 | Sanford et al. |
| 6,132,691 A | 10/2000 | Coles |

(Continued)

Primary Examiner — Monzer R Chorbaji
(74) Attorney, Agent, or Firm — St. Onge Steward Johnston & Reens LLC

(57) ABSTRACT

A disinfectant system for intracavity ultrasound probes in disclosed generally including a housing, a disinfectant chamber positioned in the housing and receiving at least one ultrasound probe, a container for containing a disinfectant solution fluidly coupled to the disinfectant chamber, at least one pump for supplying the disinfection solution from the container to the disinfection chamber and from the disinfection chamber to the container, and a controller for automated operation of the disinfectant system, wherein the disinfectant solution is a multi-use disinfectant solution. A method for disinfecting intracavity ultrasound probes is also disclosed generally including placing at least one ultrasound probe into a disinfectant chamber, supplying a disinfectant solution from a container to the disinfectant chamber via a pump, and returning the solution to the container via the pump, wherein the steps of supplying and returning the disinfectant solution are controlled by a controller.

13 Claims, 3 Drawing Sheets

(56) References Cited

U.S. PATENT DOCUMENTS

| | | | |
|---|---|---|---|
| 6,156,267 A * | 12/2000 | Pai et al. | 422/3 |
| 6,379,632 B1 | 4/2002 | Kinoshita et al. | |
| 7,641,873 B2 | 1/2010 | Coles et al. | |
| 2002/0159917 A1 | 10/2002 | Swart et al. | |
| 2005/0220665 A1 | 10/2005 | Ding | |
| 2006/0292031 A1 * | 12/2006 | Chiu et al. | 422/33 |
| 2007/0048183 A1 | 3/2007 | Nguyen et al. | |
| 2007/0207074 A1 * | 9/2007 | Jethrow | 422/292 |

\* cited by examiner

INTRACAVITY ULTRASOUND PROBE DISINFECTANT SYSTEM

FIELD OF THE INVENTION

This invention relates generally to disinfectant systems for medical devices. More specifically, the present invention relates to fully automated disinfectant systems for intracavity ultrasound probes.

BACKGROUND OF THE INVENTION

All medical instruments that come in contact with bodily fluids, such as blood, during medical procedures must be carefully disinfected to prevent harmful contamination. There are several types of disinfectants that are used to sterilize the medical instruments.

One of the common sterilization techniques used for medical devices is steam sterilization or autoclaving. This technique sterilizes medical equipment by subjecting it to high pressure steam at 121° C. or more, typically for 15 to 20 minutes depending on the size of the medical device. Typically, autoclave system includes a vacuum pump that mechanically removes the air in the sterilizer, allowing it to be more quickly replaced with saturated steam. When the steam has displaced the air, the temperature and steam pressure build until the operating temperature is reached. This operating temperature, the temperature at which sterilization occurs, is maintained for the remainder of the cycle time.

However, autoclave sterilization systems are not suitable for disinfection of heat sensitive medical devices because such devices can be destroyed or have their useful lives severely curtailed by the high temperature and pressures associated with the steam autoclave. The heat sensitive medical devices, therefore, are commonly disinfected using liquid high level disinfectants rather than the cheaper and efficient method of steam autoclaving. The two main categories of such heat sensitive instruments are endoscopes and intracavity ultrasound probes.

Endoscopes are typically disinfected in automated washing machines that disinfect and rinse the endoscopes. There are several known automated washing machines marketed by different companies.

There are several kinds of intracavity ultrasound systems that have become increasingly popular due to their efficacy in providing useful medical information in a reasonably non-invasive manner. One of such ultrasound systems is a transvaginal ultrasound that uses an internal probe, or transducer, that enters the vaginal cavity. An internal probe allows for closer access to the structures that need evaluation. With closer access, higher frequency sound waves can be used, which provides a clearer image due to better resolution. This technique is often used to evaluate suspected cancer or abnormal growths in the female reproductive system.

Another type of intracavity ultrasound that has become increasingly popular is an endorectal ultrasound, also called transrectal ultrasound. The endorectal ultrasound is a special ultrasound technique in which the transducer is directly inserted through the anus and into the patient's rectum. The sound wave echoes detected by the transducer are converted by a computer into an image.

Both vaginal and rectal ultrasound probes are examples of heat sensitive medical instruments that cannot be steam autoclaved. The current state of the art in disinfecting such probes is to manually place an ultrasound probe into a container filled with a high level disinfectant for a certain period of time, usually specified by a manufacturer of the disinfectant. This is then followed by several fresh water rinses to remove the high level disinfectant residue from the probe.

One of such systems is described in U.S. Pat. No. 6,132, 691 to Coles. This patent discloses a manual station for disinfecting intracavity ultrasound probes, such as vaginal and rectal ultrasound probes. The station includes housing and at least two containers replaceably positioned in the housing and contain a disinfectant and a rinsing agent. The ultrasonic probes are manually placed in the container with the disinfectant for soaking, and then in the container with the rinsing agent for rinsing.

However, there are a number of problems associated with known disinfecting systems for intracavity ultrasound probes. For example, one disadvantage of known systems is that the disinfecting process must be performed by an operator. The operator's variation in the performance of the process, such as mixing of the disinfectant solution, timing and equipment handling, raises problems of assurance and reproducibility of the manual disinfection process. Another disadvantage is that the system operator typically receives a prolonged exposure to harmful disinfectant fumes due to the time-consuming steps involved with the manual disinfection of the ultrasound probes. Yet another disadvantage of this known system is that it utilizes a single-use disinfectant solution, which has to be discarded after each disinfection procedure, which renders the procedure very expensive and inefficient.

What is desired, therefore, is an improved disinfectant system for intracavity ultrasound probes that overcomes the problems associated with known disinfectant systems. What is also desired is a disinfectant system for intracavity ultrasound probes that does not require manual operation by an operator thereby reducing harmful exposure to disinfectant fumes. What is further desired is a disinfectant system for intracavity ultrasound probes that is fully automated and thus more accurate. What is also desired is a disinfectant system for intracavity ultrasound probes that is capable of reusing the disinfectant solution thereby allowing for more a efficient and less costly disinfection procedure.

SUMMARY OF THE INVENTION

Accordingly, it is an object of the present invention to provide an improved disinfectant system for intracavity ultrasound probes that overcomes the problems associated with known disinfectant systems.

It is another object of the present invention to provide an intracavity ultrasound probe disinfectant system that is fully automated and more reliable.

It is a further object of the present invention to provide an intracavity ultrasound probe disinfectant system that does not require manual operation and thereby eliminates operator's exposure to harmful disinfectant fumes.

It is yet another object of the present invention to provide an intracavity ultrasound probe disinfectant system that is designed to utilize a multi-use disinfectant solution to achieve a more efficient and less expensive disinfection procedure.

In order to overcome the deficiencies of the prior art and to achieve at least some of the objects and advantages listed, the invention comprises an intracavity ultrasound probe disinfectant system including a housing, a disinfectant chamber positioned in the housing and receiving at least one ultrasound probe, a container for containing a disinfectant solution fluidly coupled to the disinfectant chamber, at least one pump for supplying the disinfection solution from the container to the disinfection chamber and from the disinfection chamber to the container, and a controller for automated operation of the disinfectant system, wherein the disinfectant solution is a multi-use disinfectant solution.

In some embodiments, the disinfectant solution is an ortho-phthalaldehyde based disinfectant solution.

In certain embodiments, the disinfectant system also includes a fluid conduit for supplying a rinsing agent to the disinfectant chamber and a drain for discarding the rinsing agent from the disinfectant chamber. In some of these embodiments, the rising agent is water. In some cases, the disinfectant system also includes a filtration system for cleansing the rinsing agent before it enters the disinfectant chamber.

In some embodiments, the disinfectant system further includes at least one holder receiving an electrical component of the at least one ultrasound probe when the probe is positioned in the disinfectant chamber.

In certain embodiments, the disinfectant system also has a plurality of valves operated by the controller.

In some embodiments, the disinfectant system further includes at least one sensor for measuring a quantity of the disinfectant solution within the disinfectant chamber. In certain of these embodiments, the controller controls the supply of the disinfectant solution to the disinfectant chamber at least partially based on the calculated quantity.

In some cases, the controller includes a processor for recording and storing ultrasound probe profile data for later retrieval by a user.

In certain embodiments, the disinfectant chamber is removably positioned in the housing.

In some of these embodiments, the disinfectant chamber has a length that is greater than a length of the at least one ultrasound probe. In some embodiments, the disinfectant chamber has an inner diameter greater than an outer diameter of the at least one ultrasound probe.

In some cases, the disinfectant system also includes a heater positioned adjacent the container for maintaining a predetermined temperature of the disinfectant solution.

In certain embodiments, the disinfectant system further has an air filtration system positioned within the housing and including an air circulation fan and an air filter for deactivating harmful odors generated by the disinfectant solution before discharging the air from the housing.

The invention also comprises a method for disinfecting intracavity ultrasound probes, including the steps of placing at least one ultrasound probe into a disinfectant chamber contained within a housing, supplying a disinfectant solution from a container to the disinfectant chamber via a pump, and returning the disinfectant solution from the disinfection chamber to the container via the pump, wherein the steps of supplying the disinfectant solution to the disinfectant chamber and returning the disinfectant solution to the container are controlled by a controller.

In some advantageous embodiments, the disinfectant solution comprises a multi-use disinfectant solution. In some of these embodiments, the disinfectant solution comprises an ortho-phthalaldehyde based disinfectant solution.

In certain embodiments, the method further includes the steps of supplying a rinsing agent to the disinfectant chamber via a fluid conduit and discarding the rinsing agent from the disinfectant chamber via a drain, wherein said steps are controlled by the controller. In some of these embodiments, the method also includes the step of filtering the rinsing agent before it enters the disinfectant chamber via a filtration system provided within the housing.

In some advantageous embodiments, the method further includes the step of securing an electrical component of the at least one ultrasound probe in at least one holder when the probe is positioned in the disinfectant chamber.

In certain embodiments, the method includes the steps of measuring a quantity of the disinfectant solution within the disinfectant chamber via at least one sensor and controlling the supply of the disinfectant solution to the disinfectant chamber via the controller at least partially based on the calculated quantity.

In some embodiments, the steps of supplying the disinfectant solution from the container to the disinfectant chamber and returning the disinfectant solution from the disinfectant chamber to the container are repeated.

In certain advantageous embodiments, the method also includes the step of testing the disinfectant solution in the container to determine a minimum effective concentration of the solution.

In some embodiments, the method further includes the step of recording and storing ultrasound probe profile data via the controller for later retrieval by a user.

Other objects of the invention and its particular features and advantages will become more apparent from consideration of the following drawings and accompanying detailed description.

DETAILED DESCRIPTION OF THE INVENTION

Figure 1:
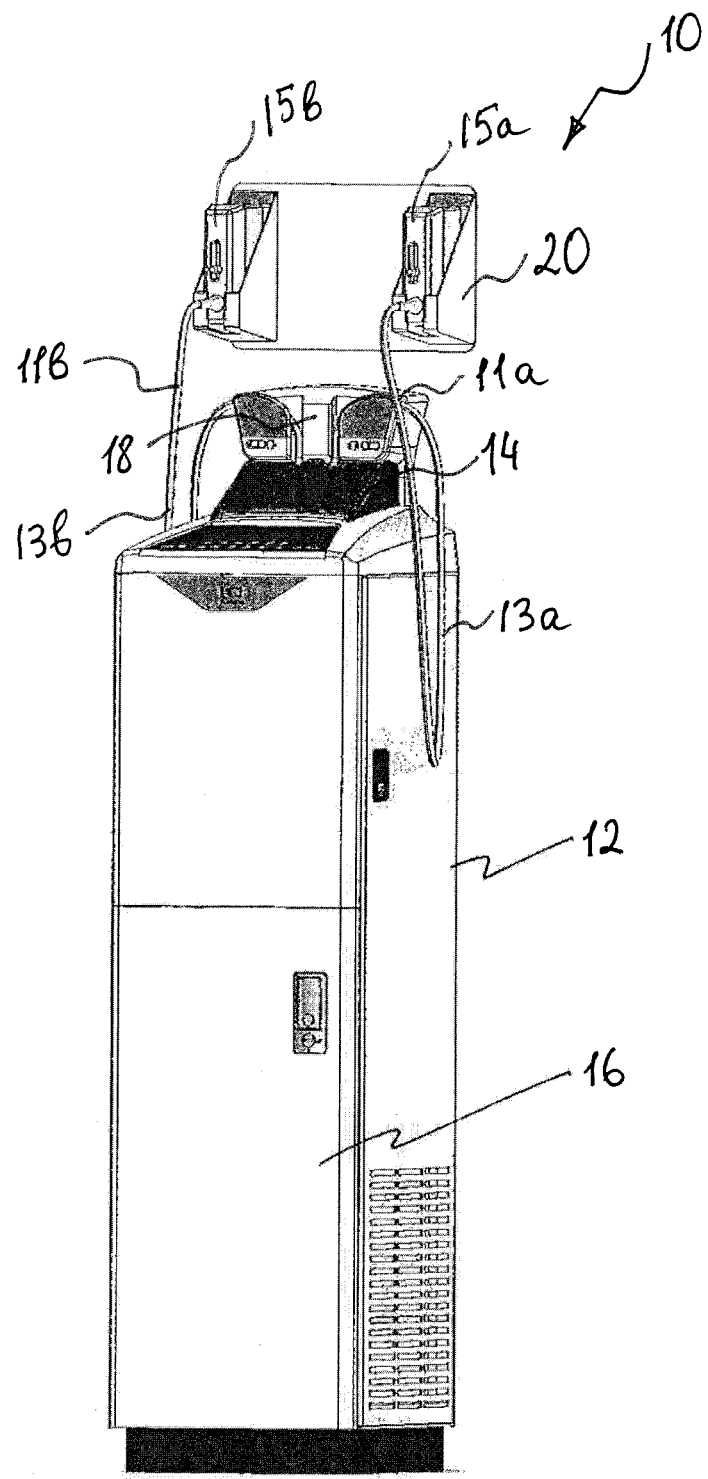
FIG. 1 is a front perspective view of a disinfectant system in accordance with the invention.

The present teachings are described more fully hereinafter with reference to the accompanying drawings, in which the present embodiments are shown. The following description is presented for illustrative purposes only and the present teachings should not be limited to these embodiments.

As used in the description, the terms "top," "bottom," "above," "below," "over," "under," "above," "beneath," "on top," "underneath," "up," "down," "upper," "lower," "front," "rear," "back," "forward" and "backward" refer to the objects referenced when in the orientation illustrated in the drawings, which orientation is not necessary for achieving the objects of the invention.

The disinfectant system of the present invention is particularly suitable for disinfecting vaginal/rectal ultrasound probes. However, it should be understood that other kinds of intracavity ultrasound probes may be disinfected using the system and method of the present invention.

The disinfectant system for vaginal/rectal ultrasound probes is a unit that encloses all the working parts in a single housing for ease of operation. The unit will preferably be placed on the floor and attached to the wall to prevent the unit from falling forwards, although other configurations are possible without departing from the spirit of the invention. The housing includes a disinfection chamber that receives at least one ultrasound probe. A container filled with a disinfectant is placed in the lower part of the housing. The ultrasound probes are suspended into the disinfection chamber and held in place by a strain relief that holds the electrical cord at a pre-determined mark. The disinfectant is pumped into the disinfection chamber. After a pre-determined time it is then pumped back into the container for further use. The probe is then rinsed with fresh water. The disinfectant system is connected to a fresh water supply and a drain via any suitable connectors, e.g. quick disconnect fittings. The fresh water supply will pass through an external water filtration system that may include a pre-filter for sediment followed by a bacteria retention filter of 0.02 microns or better.

The disinfecting process is completely automated and is managed by any suitable micro processor. The disinfectant system further includes a control panel that prompts the end user for each task involved in the disinfecting process. The micro processor records and saves information pertinent to an ultrasound probe to be disinfected, such as the probe ID number, date and time of disinfecting procedure and an outcome of the disinfection cycle. This information may be later retrieved from the system by the end user.

The disinfectant system of the present invention may be used with any suitable type of disinfectant solution. Preferably, the disinfectant is an FDA approved high-level disinfectant that is also approved by an ultrasound probe manufacturer for use with their specific ultrasound probes. One of the advantages of such disinfectants is that they may be reused, therefore allowing for significant cost savings for the end user. In one advantageous embodiment, the disinfectant system of the present invention is used with an ortho-phthalaldehyde (OPA) based disinfectant solution, which may be reused for up to twenty-eight days.

One advantageous embodiment of the present invention is illustrated in FIG. 1. Although the invention has been described with reference to a particular arrangement of parts, features and the like, these are not intended to exhaust all possible arrangements or features, and indeed many other modifications and variations will be ascertainable to those of skill in the art.

As shown in FIG. 1, the intracavity ultrasound probe disinfectant system (10) includes a housing (12), which contains all of the components of the system. The housing (12) includes an upper access point (14), such as a door, and a lower access point (16). In the embodiment shown in this figure, the housing (12) is placed directly on the floor and may be further attached to the wall to prevent the unit from falling forward. However, it should be understood that other configurations, such as suspending the unit from the wall, are possible without departing from the spirit of the invention.

The disinfectant system (10) of the present invention is designed to accommodate one or more ultrasound probes. FIG. 1 illustrates the disinfectant system (10) with two ultrasound probes (11a, 11b) in place. It is understood that the disinfectant system may accommodate only one ultrasound probe, or more than two ultrasound probes, in accordance with the present invention. Each of the ultrasound probes (11a, 11b) has a cord section (13a, 13b), a probe section (not shown), and an electrical connector (15a, 15b).

As depicted in FIG. 1, the housing (12) also includes a strain relief (18) positioned above the upper door (14). The strain relief (18) has a curved shape to accommodate the placement of the probe cord section (13a, 13b). However, any other suitable shape of the strain relief may be utilized, depending on a particular type of the ultrasound probe being disinfected. The strain relief (18) operates to engage the cord (13a, 13b) to prevent it from slipping out.

A holder (20) is also provided for accommodating the electrical connector sections (15a, 15b) of the ultrasound probes (11a, 11b). The holder (20) is placed outside of the housing (12) to protect the electronics and prevent any exposure to the disinfectant solution. In the embodiment shown, the holder (20) is attached to a wall adjacent the housing (12). It is noted, however, that the holder (20) may be attached to an outside wall of the housing (12) adjacent the strain relief (18).

The disinfectant system (10) may also include a cable sensor positioned adjacent to the strain relief (20) for sensing whether the probe cord (13a, 13b) is positioned in the strain relief (20).

Figure 2:
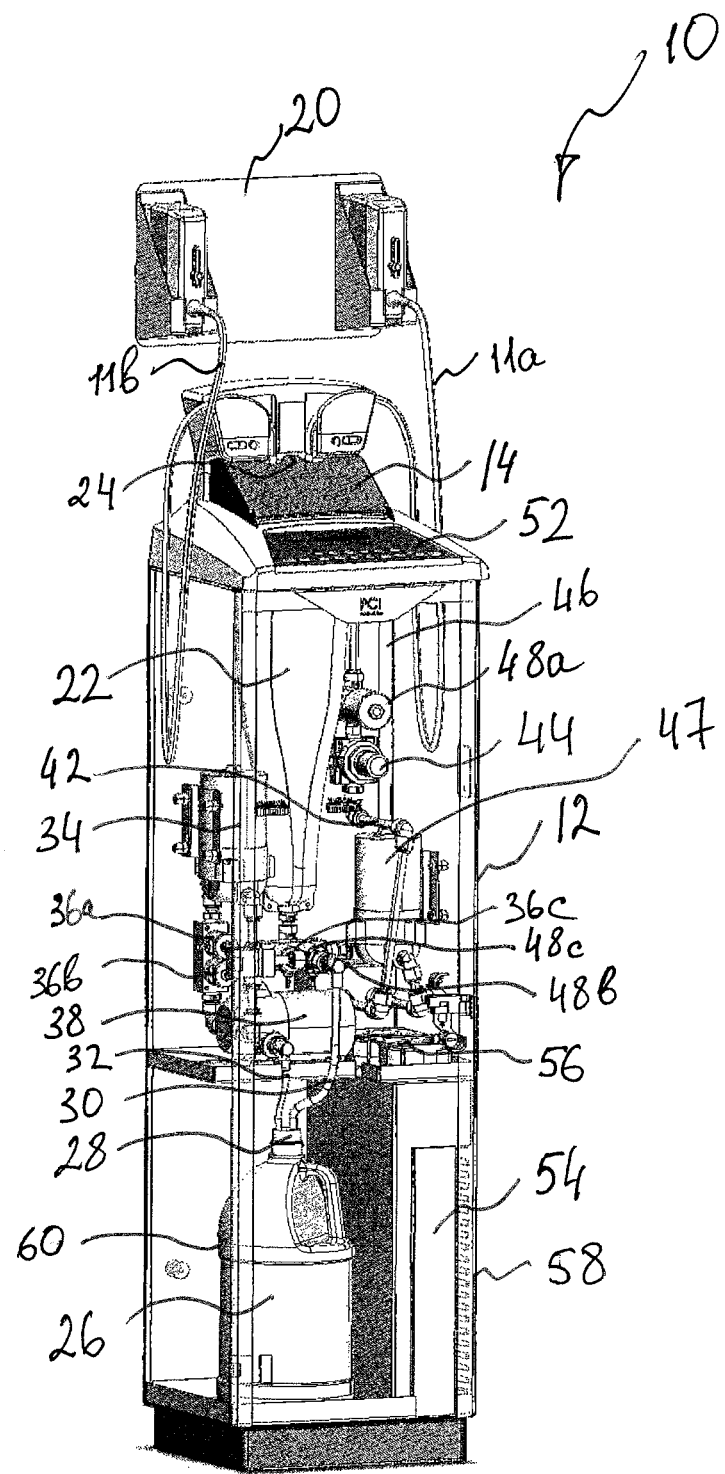
FIG. 2 is front perspective view of the disinfectant system of FIG. 1, showing the interior components of the system.
Figure 3:
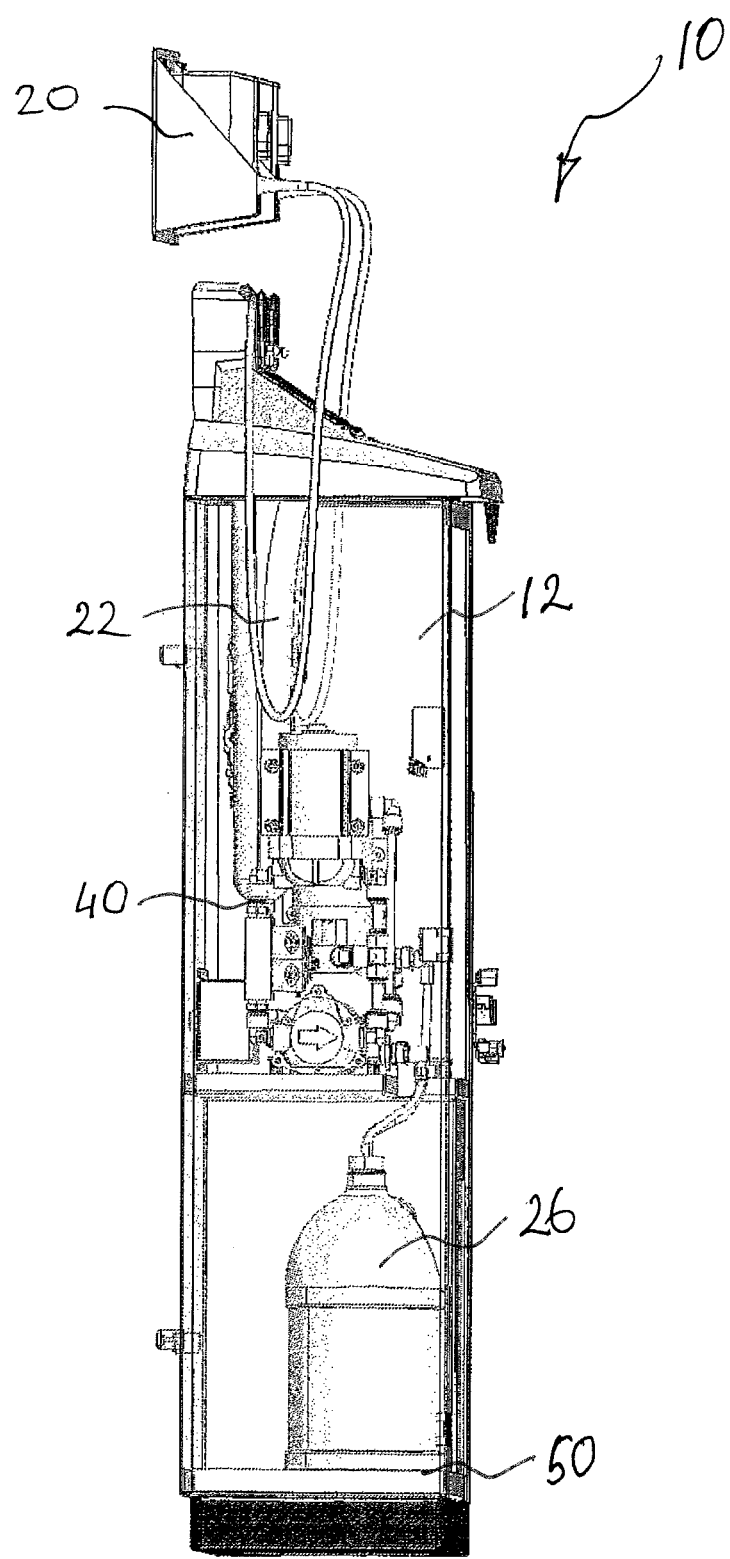
FIG. 3 is a side, partially cross-sectional view of the disinfectant system of FIG. 1.

FIGS. 2 and 3 illustrate the disinfectant system (10) of the present invention with the interior components of the housing (12) shown. The housing (12) contains a disinfection chamber (22) removably positioned in the upper part of the housing (12) and adapted for receiving at least one ultrasound probe (11a, 11b). It is envisioned that the disinfection chamber (22) may be removed from the housing (12) and replaced by a different disinfection chamber to accommodate different types of ultrasound probes. The housing (12) is shown with two ultrasound probes (11a, 11b) supportingly positioned within the disinfection chamber (22). As discussed above, it is understood that the disinfectant system (10) of the present invention may allow for simultaneous disinfection of one or two or more intracavity ultrasound probes.

The disinfection chamber (22) may comprise a wide variety of shapes to accommodate the shape of the intracavity ultrasound probes (11a, 11b) to be inserted therein. Preferably, the disinfection chamber (22) has an overall length greater than the length of the ultrasound probes (11a, 11b), and a diameter greater than the diameter of at least two ultrasound probes (11a, 11b) to allow for easy insertion of one or more probes into the chamber. In one advantageous embodiment, the disinfection chamber (22) has a cylindrical shape designed to accommodate vaginal/rectal ultrasound probes, which are typically approximately 12" long and are made of a rigid plastic.

The disinfection chamber (22) may be formed from any commercially acceptable material, e.g. high-density polyethylene. The disinfection chamber (22) may include a removable basket (not shown) to allow the user to place loose items, e.g. biopsy guides, that require disinfection to be disinfected at the same time as the ultrasound probe. The disinfection chamber (22) terminates in the upper access point or door (14), through which the ultrasound probes (11a, 11b) are introduced into the chamber (22). The upper door (14) may be opened to allow the operator to insert the probes (11a, 11b) into the chamber (22), and then closed. The upper door (14) is provided with a sensor (24) that confirms that the upper door is open or closed. The disinfection chamber (22) may further include a plurality of sensors positioned inside the chamber (22) for sensing a quantity of a disinfectant solution within the chamber, as well as rinse level and overflow level. Any type of suitable sensors may be used in accordance with the present invention.

The disinfectant system (10) of the present invention further includes a container (26) removably placed in the lower portion of the housing (12). The container (26) contains a disinfectant solution and may be of any commercially available size and shape. In one advantageous embodiment, the container (26) is a one gallon bottle of an ortho-phthalaldehyde (OPA) high level disinfectant solution. The container (26) may include a screw cap and protective foil to prevent contamination and/or spillage of the disinfectant solution before use.

The container (26) is provided with a plug assembly (28) for removable attachment of the container (26) to the other components of the disinfectant system (10). The plug assembly (28) may include a plug made from any suitable material, such as rubber, that tightly fits into an opening in the container (26). The plug assembly (28) may further include a rod that extends into the container (26) when inserted. The rod may be made from any suitable material, e.g. stainless steel. The plug may further include an air release vent to expel an excess of air that may accumulate in the container (26). The plug assembly (28) also includes a connection or fitting to allow the operator to quickly and easily connect and disconnect the container (26) from the disinfectant system (10).

Once the container (26) is positioned within the housing (12) through the lower door (16), it is connected to a conduit leading to the disinfection chamber (22) via the plug assembly (28). As depicted in FIG. 2, the conduit includes a disinfectant supply line (30) and a disinfectant drain line (32). The supply line (30) and the drain line (32) are made from any suitable material and may have different diameters and lengths depending on the size of the housing (12).

The disinfectant supply line (30) functions to supply the disinfectant solution from the container (26) to the disinfection chamber (22). A pump (34) is connected to the supply line (30) for pumping the disinfectant solution from the container (26) through valves (36a, 36c) to the disinfection chamber (22). Any suitable commercially available pump may be used in accordance with the present invention. The valves (36a, 36c) may be any suitable valve type, e.g. solenoid valve. The valves operate to open and close the supply line (30) during the disinfection cycle.

The drain line (32) connects the bottom portion of the disinfection chamber (22) with the container (26) and functions to drain the disinfectant solution from the chamber through valves (36c, 36b) back to the container (26) for reuse. A pump (38) is placed in the drain line (32) for pumping the disinfectant solution from the disinfection chamber (22) back to the container (26). As shown in FIG. 3, a liquid filter screen (40) may be positioned in the bottom of the disinfection chamber (22) to prevent any debris from blocking the valves (36c, 36b) and the pump (38) as the disinfectant solution drains from the chamber. The valves (36b, 36c) may be any suitable valve type, e.g. solenoid valve. The valves operate to open and close the drain line (32) during the disinfection cycle.

As shown in FIG. 2, the disinfectant system (10) further includes a water supply line (42) connected to an external water supply. The water supply line (42) is connected to a water pressure regulator (44) and then to the disinfection chamber (22). The pressure regulator (44) functions to regulate the water pressure within the line (42). Any known suitable type of pressure regulator, such as a valve, may be used in accordance with the present invention.

Two valves (48a, 48c) are positioned in the water supply line for opening and closing the line during the rinse cycle. In one possible embodiment, the water supply line (42) is connected to the external water line via quick disconnect fitting or any other suitable connector. The disinfectant system (10) further includes a water drain line (46) connected to an external drain. The water drain line (46) includes a pump (47) for pumping the water out of the disinfection chamber (22) during the rinse cycle through the valves (48b, 48c). As discussed above, any suitable type of valves and pumps can be used without departing from the spirit of the present invention.

As depicted in FIG. 3, the disinfectant system (10) of the present invention also includes one or more heating devices to heat the disinfectant solution to an optimal desired temperature. For example, a heating pad (50) may be positioned underneath the container (26) for heating the disinfectant solution contained therein. Temperature sensors may also be provided on the container (26) and the disinfectant chamber (22) for measuring the temperature of the disinfectant solution.

In accordance with one advantageous embodiment of the present invention, the disinfection process performed by the disinfectant system is fully automated and is controlled by a computer based electronic control system. As shown in FIG. 2, all components of the intracavity ultrasound disinfectant system (10) are activated and controlled by a control panel (52) provided on the top surface of the housing (12) and including a central processing unit (CPU). The system may further include a display mounted on the panel (52) for displaying information to the user. The control panel (52) includes a keypad to allow the user to input information, such as an ultrasound probe identification number, time and date. Any information inputted into the disinfection system by the user, as well as any information about the disinfection cycle, can be accessed and retrieved from the system at a later time. In some embodiments, the information may be downloaded by the user via any suitable memory device, such as a flash memory card, through a port (not shown) provided in the housing (12).

If desired, various sensors may be included in the disinfectant system (10) in accordance with the present invention to ensure proper operation of the system. For example, in the embodiment depicted in the figures, a sensor (60) may be positioned adjacent the container (26). This sensor operates to confirm that the container (26) is placed in the housing (12) before the commencement of the disinfecting cycle. Similarly, a sensor may be provided in the upper portion of the housing (12) adjacent the strain relief (18) to detect the ultrasound probe cords (13a, 13b) positioned in the housing. Additionally, as depicted in FIG. 2, the sensor (24) is provided in the upper door (14) for sensing an opened or closed position of the door. Any known suitable types of sensors may be used in accordance with the present invention.

In one advantageous embodiment of the present invention shown in FIG. 2, the housing (12) is further provided with an air filtration system, which may incorporate air filters (54) that function to deactivate and remove harmful fumes generated by the disinfectant solution. The housing (12) also includes one or more exhaust fans (56) provided in the housing wall. The exhaust fans (56) are utilized to draw the vapor through the filter (54) before recirculating the filtered vapor into the ambient surroundings through an opening (58) in the housing wall.

One advantageous embodiment of the automated operation of the intracavity ultrasound probe disinfectant system of the present invention is described below. It would be appreciated by those skilled in the art that various changes and modifications can be made to the described embodiment without departing from the spirit of the present invention. All such modifications and changes are intended to be covered hereby.

The disinfectant system (10) is first plugged into an electric outlet. The user may mark the ultrasound probes according to an operator's manual to ensure that the probes are at the correct position for disinfection.

To prepare the disinfectant system for operation, the user will remove a closure system, such as a screw cap and protective foil, from a container (26) of disinfectant solution and replace it with the plug assembly (28). The plug assembly (28) is inserted into the opening in the container (26) and is tightly fitted therein via a plug. At least one rod is extended from the plug assembly (28) into the disinfectant solution in the container (26). Next, the user may place the container (26) with the plug assembly (28) into the lower portion of the housing (12) through the lower door (16). The plug assembly (28) is then connected to the internal plumbing via the fitting.

The disinfectant system (16) is then be switched ON using the ON/OFF switch positioned on the wall of the housing (12). Switching on the system activates several operations. First, the control panel (52) will prompt the user to enter information regarding the disinfectant solution, such as an expiry date for the solution. The expiry date is the date the disinfectant solution must be discarded from the system. This prompt may appear only when a new container of disinfectant solution is inserted. Then, the sensor (60) will sense that a container of disinfectant (26) has been placed in the housing (12). Next, the lower heat pad (50) may be turned on to maintain a desired temperature of the disinfectant solution within the container (26). At this point, the air filtration system, such as the fan (56), is turned on to filter the disinfectant vapor through the filter (54) before it exits the housing (12). The fan (56) may operate continuously when the system is powered up.

The control panel (52) will then indicate to the user that the system is ready for operation, for example, by showing 'Ready for Use: Press Enter' on the display. The control panel (52) will prompt the user to enter information relating to the ultrasound probe to be disinfected, such as the probe identification number. In one possible embodiment, each ultrasound probe that will be placed into the disinfectant system (10) will have a unique digit identification number. The CPU may also automatically record the time and date, and may also record whether or not there was a successfully completed disinfection cycle. All recorded information will be stored and may be later retrieved by the user via the data port provided in the housing wall. The disinfection system (10) may also utilize an emergency back-up battery to maintain the recorded information.

Next, the control panel (52) will prompt the user to open the upper door (14). The sensor (24) will confirm that the door is open and will prompt the user to insert the ultrasound probes (11a, 11b). The user will then place the electrical connectors (13a, 13b) of the ultrasound probes into the holder (20), and will then place the ultrasound probes (11a, 11b) into the disinfection chamber (22). The probes are inserted into the disinfection chamber (22) and the electrical cords (13a, 13b) are placed over the curved strain relief (18). The user may align a mark provided on the electrical cords with a mark provided on the strain relief to ensure that the probes are suspended to the correct height. The strain relief (18) prevents the cords (13a, 13b) from slipping. The sensor provided on the strain relief (18) confirms the cords are in place. The disinfectant system (10) will not start without this step, and if the ultrasound probes (11a, 11b) are removed prior to the end of the disinfection cycle, the system will go into an 'Abort Cycle,' described below.

After placing the ultrasound probes (11a, 11b) in the disinfection chamber (22), the user will close the upper door (14), and press the START button to initiate the full cycle. The pump (34) will then turn on and pump the disinfectant solution from the container (26) into the disinfectant chamber (22). A sensor positioned in the chamber (22) will sense that a desired level of the disinfectant is reached within the chamber, which turns off the pump (34). In one advantageous embodiment, a temperature sensor also positioned in the chamber (22) may confirm that the minimum required temperature of the disinfectant solution has been satisfied. The pre-determined disinfection period may not start unless the temperature is satisfied.

In certain advantageous embodiments, the control panel (52) will then prompt the user to conduct a minimum effective concentration test (MEC test) to confirm the efficacy of the disinfectant solution. This test is performed by utilizing a proprietary test strip. The door lower (16) is opened and the test strip is dipped into the disinfection solution. Note that the display will show 'Close Door' when the door is opened during this process. The test strip is then compared to a color chart provided by the manufacturer to establish efficacy of the disinfectant solution.

The disinfectant solution will remain in the disinfection chamber (22) for a predetermined amount of time. After the predetermined disinfection time, the valves (36b, 36c) will open, the pump (38) will be turned on, and the disinfectant solution will be pumped back into the container (26). A current detector on the pump (38) will sense the lower current draw of the pump, meaning that all liquid has been discharged from the disinfection chamber (22) and will stop pumping and close valves (36b, 36c).

After the disinfection cycle, the ultrasound probes (11a, 11b) are rinsed with a rinsing agent, such as fresh water, to ensure that no residual levels of disinfectant are left on the probes. Immediately after the valves (36b, 36c) close following the disinfection cycle, the valves (48a, 48c) will open. Another sensor positioned within the disinfection chamber (22) will sense the correct rinse water level in the chamber (22). In certain advantageous embodiments, the level of the rinse water in the chamber (22) is higher than the disinfectant solution level. The system will then turn off the valves (48a, 48c). The rinse water will remain in the disinfection chamber (22) for a pre-determined amount of time. After this time, valve (48c, 48b) will open and pump (47) will pump the water to drain via drain line (46). A current detector on pump (47) will sense the lower current draw of the pump, meaning that all liquid has been discharged from the disinfection chamber and will stop pumping and close valves (48c, 48b). In one advantageous embodiment, the rinsing cycle is repeated three times to ensure that the ultrasound probes are completely rinsed off. This will complete the disinfection and rinse cycles.

The control panel (52) will then inform the user that the disinfection cycle is completed. For example, an 'end of cycle' message may be displayed on the control panel (52), and/or the user may be alerted by a flashing light or a sound. The alert signal may continue until the ultrasound probes (11a, 11b) are removed from the housing (12). The sensor positioned adjacent the strain relief will signal to the CPU that the probes have been removed, and the control panel (52) will inform the user that the disinfection system is ready for further use, e.g. by displaying a 'Ready for Use' message on the display. The ultrasound probes may be left in the disinfectant system (10) until needed.

The following is a description of an exemplary method of operation of the intracavity ultrasound probe disinfectant system (10) in accordance with one advantageous embodiment of the present invention.

Preparation
Factory Set Up:
1. Enter Date: Month/Day/Year.
2. Enter Time: Hour/Minute.
3. Save Settings.
Customer Set Up:
1. Measure and mark each probe's electrical cord according to instructions in operators manual to ensure proper positioning of probe in a disinfection chamber (22).
2. Plug the system into 110V outlet.
3. Enter disinfection time for a disinfectant solution.
Prepare for Use:
1. Remove a cap from a container with disinfectant solution (26).
2. Insert a plug assembly (28) into the container.
3. Open a lower door (16).
4. Place the opened container (26) with the plug assembly (28) into the housing (12).

5. Connect to a fitting.
6. Close the lower door (16).
7. Switch the system ON, using ON/OFF switch. Following actions happen when the system is switched on:
   a. A sensor (60) confirms that a full container (26) is in place. The system will not begin operating without this step.
   b. A heat pad (52) is energized to maintain a pre-determined temperature using a built-in thermocouple.
   c. Two fans (56) turn on and stay on as long as the system is powered up.
   d. A control panel (52) shows 'Ready for Use: Press Enter.'

Unit Ready to Receive Probe:
1. Enter Probe ID into the control panel (52).
2. The system automatically records time and date. Battery back-up is provided for time and date.
3. Open an upper door (14).
4. Place electrical connectors (15a, 15b) into an electrical connector holder (20).
5. Place ultrasound probes (11a, 11b) into the disinfection chamber (22).
6. Place electrical cords (13a, 13b) of the probes (11a, 11b) over a strain relief (18)
7. A sensor confirms the cords in place. The system will not begin operating without this step. The system will abort if the cord is removed before end of the cycle.
8. Close the upper door (14). A sensor (24) confirms that the door is closed.
9. Press START on the control panel (52). Start button is lighted.

Disinfection Cycle
Operation 1:
1. A pump (47) turns ON, valves (48b, 48c) open and the system runs a five second purge cycle.
2. A pump (34) turns ON, valves (36a, 36c) open, disinfectant solution is pumped into the disinfection chamber (22).

Operation 2:
3. A sensor senses that a proper level of the disinfectant solution is reached in the chamber (22).
4. The pump (34) turns OFF and valves (36a, 36c) close.
5. A thermocouple reads temperature of the disinfectant solution in the chamber (22). The temperature must exceed the minimum required temperature of the disinfectant to initiate the minimum soak time.
6. The minimum soak time starts after confirmation of the desired temperature and level is achieved.
7. The control panel (52) prompts the user to conduct a minimum effective concentration test with a test strip.

Operation 3:
8. After a pre-determined soak time a valves (36c, 36b) OPEN.
9. A pump (38) pumps the disinfectant solution back to the container (26).
10. Current sensor on the pump (38) senses low current indicating liquid has been removed from chamber (22).
11. Time delay to allow the liquid to drain to the container (26).
12. The pump (38) stops.
13. The valves (36c, 36b) CLOSE.

Rinse/Drain Cycle
Operation 1:
1. The valves (48a, 48c) OPEN allowing fresh water to flow into the disinfection chamber (22).
2. The sensor senses water fill level in the chamber (22), which is to be higher than the level of the disinfectant solution.
3. The valves (48a, 48c) CLOSE.
4. Rinse water remains in chamber (22) for pre-determined period.
5. The valves (48b, 48c) OPEN.
6. The pump (47) turns ON pumping rinse water to drain.
7. The valves (48b, 48c) CLOSE.
8. Current sensor on the pump senses low current indicating water has been removed from chamber (22) and turned off pump (47).
9. This process is repeated three times.

End of Cycle
1. Display shows 'End of Cycle' and emits beep and flashing light to alert the end user that the ultrasound probe is ready. This step will continue until the probes are removed from the chamber (22).
2. Sensor provided on the strain relief (18) tells the CPU that the probes (11a, 11b) are removed and the display will show 'Ready for Use: Press Enter'.
3. Information about the cycle is stored in the CPU and can be accessed by the user via a memory stick.

The disinfectant system of the present invention may incorporate various safety features to ensure a safe operation by the end user. If the level of the disinfectant solution in the chamber (22) exceeds the normal level, the sensor provided in the chamber (22) will stop the system and show an error code on the display. This will require the operator to push the 'Abort' button, which will open valves (36c, 36b) and turn on pump (38) and pump disinfectant back to the container (26). The disinfection chamber (22) is preferably designed to hold approximately fifty percent less liquid than the disinfectant container (26).

The one advantageous embodiment, the disinfectant system (10) may include an abort cycle. In the event that the sensors detect any kind of malfunction in the system, the disinfection system will flash an 'Error Code, Service Required' on the display and give an audible alarm. End user will call manufacturer to review Error Code, and then push the 'Abort' key. Depending on which cycle the device is in (i.e. disinfection or rinse), the disinfection solution will be returned to the container (26) or the rinse water will be pumped to drain. These steps may be then followed by a full rinse cycle described above. At the end, the display will exhibit an 'Abort Cycle Completed' message. In order to proceed with the disinfection cycle, the operator will need to remove the ultrasound probes (11a, 11b) from the housing (12) and then repeat all of the steps of the cycle described above.

It would be appreciated by those skilled in the art that various changes and modifications can be made to the illustrated embodiment without departing from the spirit of the present invention. All such modifications and changes are intended to be covered hereby.

What is claimed is:
1. A method for disinfecting intracavity ultrasound probes, comprising the steps of:
   placing at least one ultrasound probe into a disinfectant chamber contained within a housing;
   supplying a disinfectant solution from a container placed in said housing to said disinfectant chamber via a pump; and
   returning the disinfectant solution from said disinfection chamber to the container via said pump after completion of a disinfection phase;

wherein the steps of supplying the disinfectant solution to said disinfectant chamber and returning the disinfectant solution to the container are controlled by a controller.

2. The method of claim 1, wherein the disinfectant solution comprises a re-usable pre-activated disinfectant solution.

3. The method of claim 1, wherein the disinfectant solution comprises an ortho-phthalaldehyde based disinfectant solution.

4. The method of claim 1, wherein the disinfectant solution comprises a hydrogen peroxide based disinfectant solution.

5. The method of claim 1, wherein said pump comprises a connector with at least one first line for fluid transfer to said disinfection chamber and at least one second line for fluid transfer from said disinfection chamber to said container.

6. The method of claim 1, further comprising the steps of supplying a rinsing agent to said disinfectant chamber via a fluid conduit and discarding the rinsing agent from said disinfectant chamber via a drain, wherein said steps are controlled by said controller.

7. The method of claim 6, further comprising the step of filtering the rinsing agent before it enters said disinfectant chamber via a filtration system provided within said housing.

8. The method of claim 1, further comprising the steps of measuring a quantity of the disinfectant solution within said disinfectant chamber via at least one sensor and controlling the supply of the disinfectant solution to said disinfectant chamber via said controller at least partially based on the calculated quantity.

9. The method of claim 1, wherein the steps of supplying the disinfectant solution from the container to said disinfectant chamber and returning the disinfectant solution from said disinfectant chamber to the container are repeated.

10. The method of claim 1, further comprising the step of testing the disinfectant solution in the container to determine a minimum effective concentration of the solution.

11. A method for disinfecting intracavity ultrasound probes, comprising the steps of:
    placing at least one ultrasound probe into a disinfectant chamber contained within a housing;
    supplying a disinfectant solution from a container placed in said housing to said disinfectant chamber via a pump;
    returning the disinfectant solution from said disinfection chamber to the container via said pump, wherein the steps of supplying the disinfectant solution to said disinfectant chamber and returning the disinfectant solution to the container are controlled by a controller; and
    deactivating harmful odors generated by the disinfectant solution via an air filtration system comprising an air circulation fan and an air filter before discharging the air from said housing.

12. A method for disinfecting intracavity ultrasound probes, comprising the steps of:
    placing at least one ultrasound probe into a disinfectant chamber contained within a housing;
    supplying a disinfectant solution from a container placed in said housing to said disinfectant chamber via a pump;
    returning the disinfectant solution from said disinfection chamber to the container via said pump, wherein the steps of supplying the disinfectant solution to said disinfectant chamber and returning the disinfectant solution to the container are controlled by a controller; and
    securing an electrical component of said at least one ultrasound probe in at least one holder when said probe is positioned in said disinfectant chamber.

13. A method for disinfecting intracavity ultrasound probes, comprising the steps of:
    placing at least one ultrasound probe into a disinfectant chamber contained within a housing;
    supplying a disinfectant solution from a container placed in said housing to said disinfectant chamber via a pump;
    returning the disinfectant solution from said disinfection chamber to the container via said pump, wherein the steps of supplying the disinfectant solution to said disinfectant chamber and returning the disinfectant solution to the container are controlled by a controller; and
    recording and storing ultrasound probe disinfection profile data via said controller for later retrieval by a user.

* * * * *